United States Patent [19]

Bonaventura et al.

[11] Patent Number: 5,349,054
[45] Date of Patent: Sep. 20, 1994

[54] ACTIVATED BENZENEPENTACARBOXYLATE-CROSS-LINKED LOW OXYGEN AFFINITY HEMOGLOBIN

[75] Inventors: Joseph Bonaventura; Marius Brouwer; Robert E. Cashon, all of Beaufort, N.C.

[73] Assignee: Duke University, Durham, N.C.

[21] Appl. No.: 745,587

[22] Filed: Aug. 15, 1991

[51] Int. Cl.$^5$ .................... A61K 37/00; A61K 35/14; A61K 37/02; C07K 13/00
[52] U.S. Cl. .................................... 530/385; 530/410
[58] Field of Search ...................... 530/385; 514/6

[56] References Cited

U.S. PATENT DOCUMENTS 4,061,736  12/1977  Morois et al. .................. 530/385

OTHER PUBLICATIONS

C. R. Acad. Sci Paris t 277 (Sep. 17, 1973), 963–66 R. Banerjee and A. Desbois "Effet des Avions Polycarboxylate sur henioqohire".
Shimizu et al., *Biochemistry* 13:809–813 (1984).
Walder et al., *Biochemistry* 18:418–426 (1979).
Snyder et al., *Proc. Natl. Acad. Sci. USA* 84:7280–7284 (1987).
Bucci, E. et al., *J. Biol. Chem.* 264:6191–6195 (1989).
Chang et al., In: Chang, TMS et al., ed., *Blood Substitutes,* Marcel Dekker, Inc., New York, 1989, pp. 11–29.
Venuto, In: Chang, TMS et al., ed., *Blood Substitutes,* Marcel Dekker, Inc., New York, 1989, pp. 77–83.
Chang et al., In: Chang, TMS et al., ed., *Blood Substitutes,* Marcel Dekker, Inc., New York, 1989, pp. 205–215.
Kavanaugh et al., In: Chang, TMS et al. ed., *Blood Substitutes,* Marcel Dekker, Inc., New York, 1989, p. 637.
Keipert et al., In: Chang, TMS et al., ed., *Blood Substitutes,* Marcel Dekker, Inc., New York, 1989, pp. 643–645.
Vandegriff et al., In: Chang, TMS et al., ed., *Blood Substitutes,* Marcel Dekker, Inc., New York, 1989, pp. 647–649.

Manning et al., *Proc. Natl. Acad. Sci. USA* 88:3329–3333 (1991).
Hess et al., *J Appl Physiol* 70:1639–1644 (1991).
Przybelski et al., *J Lab Clin Med* 117:143–151 (1991).
Hess et al., *Biomater Artif Cells Artif Organs* 17:632 (1989).
Marini et al., *Biomater Artif Cells Artif Organs* 17:538 (1989).
Jones et al., *Biomater Artif Cells Artif Organs* 17:643 (1989).
Kavanaugh et al., *Biomatr Artf Cells Artif Organs* 15:368 (1987).
Benesch, *Biochem. Biophys. Res. Comm.* 156:9–14 (1988).
MacDonald et al., *Biomater. Artif. Cells Artif. Organs* 18:263–282 (1990).
Clifford et al., *Biomater. Artif. Cells Artif. Organs* 18:321–328 (1990).
Greenburg, *Biomater. Artif. Cells. Artif. Organs* 16: 71–75 (1988).
Sehgal et al., *Surgery* 95:433–438 (1984).
Shimizu and Bucci, "Allosteric Effectors of Hemoglobin. Interaction of Human Adult and Fetal Hemoglobins with Poly(carboxylic acids)", Biochemistry 13:809–814 (1974).
Banerjee and Desbois, "Effect of polycarobxylate anions on hemoblobin", C. R. Acad. Sc. Paris 227 (Series D): 963–966 (English translation (pp. 1–7) of French article].

*Primary Examiner*—Howard E. Schain
*Assistant Examiner*—P. Lynn Touzeau
*Attorney, Agent, or Firm*—Pennie & Edmonds

[57] ABSTRACT

The invention is directed to a stroma-free tetrameric mammalian hemoglobin which is crosslinked with benzenepentacarboxylate, in which the crosslinking is carried out by a method comprising the step of activating at least two carboxylate groups of the benzenepentacarboxylate with an activating agent prior to reaction with the hemoglobin as well as methods for its production. Crosslinked stroma-free hemoglobin produced by methods of the present invention may be used in applications requiring physiological oxygen carriers such as in blood substitute solutions, or as in a plasma expander.

17 Claims, 12 Drawing Sheets

| CONDITION | LANE | BPC/EDC |
|---|---|---|
| +7.5mM BPC | 1<br>2<br>3<br>4 | 1/2<br>1/4<br>1/6<br>1/10 |
| +3.0mM BPC | 5<br>6<br>7<br>8 | 1/1<br>1/2<br>1/3<br>1/5 |
| +1.5mM BPC | 9<br>10<br>11<br>12<br>13 | 1/0<br>1/1<br>1/2<br>1/3<br>HbA, NOT MODIFIED |

FIG. 4B

ACTIVATED BENZENEPENTACARBOXYLATE-CROSSLINKED LOW OXYGEN AFFINITY HEMOGLOBIN

FIELD OF THE INVENTION

The invention is directed to a stroma-free tetrameric mammalian hemoglobin which is crosslinked with benzenepentacarboxylate, in which the crosslinking is carried out by a method comprising the step of activating at least two carboxylate groups of the benzenepentacarboxylate with an activating agent prior to reaction with the hemoglobin. The invention also provides methods for production of such hemoglobin. Crosslinked stroma-free hemoglobin produced by methods of the present invention may be used in applications requiring physiological hemoglobin-based oxygen carriers such as in blood substitute solutions, or as in a plasma expander.

BACKGROUND OF THE INVENTION

BLOOD SUBSTITUTES

Transfusion of a patient with donated blood has a number of disadvantages. Firstly, there may be a shortage of a patient's blood type. Secondly, there is a danger that the donated blood may be contaminated with infectious agents such as hepatitis viruses, cytomegalovirus, Epstein-Barr virus, serum parvoviruses, syphilis, malaria, filariasis, trypanosomiasis, babsiosis, pathogenic bacteria, and HIV (Bove, 1986, Progr. Hematol. 14:123–145). Thirdly, donated blood has a limited shelf life.

An alternative to transfusion involves the use of a blood substitute. A blood substitute is an oxygen carrying solution that also provides the oncotic pressure necessary to maintain blood volume. Two types of substitutes have recently been studied, fluorocarbon emulsions and hemoglobin solutions.

Fluorocarbons however are not feasible blood substitutes, since they are known at times to block the natural immune system (Dellacherie, 1986, Crit. Rev. Ther. Drug Carriers 3:41–94). In addition, the use of fluorocarbons is limited to situations in which high partial pressures of oxygen can be administered. They do not have a sufficiently high oxygen binding capacity for use under normal physiological conditions.

Hemoglobin as it exists within the red blood cell is composed of two alpha-like globin chains and two beta-like globin chains, each with a heme residue. One alpha-like globin chain and one beta-like globin chain combine to form a dimer which is very stable. Alpha-like and beta-like globin genes are each a family of related globin genes which are expressed at different stages of development and regulated by oxygen tension, pH, and the development from embryo to fetus to newborn. Two dimers then line up in antiparallel fashion to form tetramers. The binding of dimers to form the tetramers is not as strong as in the case of monomers binding to associate into dimers. The tetramers, therefore, have a tendency to fall apart to form dimers and there is always an equilibrium between tetramers, dimers, and monomers. At high concentrations of globin, the predominant form is the tetramer; with dilution, the dimer becomes the predominant form. This equilibrium is also affected by solvent, salts, pH and other factors as the forces binding the monomers together are primarily electrostatic.

Hemoglobin may exist under two conformations, the oxygenated (R-form) or deoxygenated (T-form). The deoxy structure is stabilized by the formation of salt bridges involving definite amino and carboxylic groups of globins.

The oxygen binding characteristics of hemoglobin can be characterized by a curve, called the oxygen affinity curve, obtained by plotting the fractions of available hemoglobin sites saturated with oxygen as a function of the partial pressure of oxygen in equilibrium with the solution. Information may be obtained from such plots regarding the cooperativity of oxygen binding to hemoglobin using the following Hill equation:

$$Y/1-Y = K[O_2]^n$$

where Y is the fraction of sites occupied by oxygen and n and K are adjustable constants. When the cooperativity of the oxygen binding to hemoglobin is modified, this results in a decrease of the Hill Coefficient (n). Therefore, the value of the Hill coefficient can be considered as a useful reflection of the efficacy of the oxygen-carrying function. The oxygen affinity of hemoglobin may also be characterized by determining the $P_{50}$, which is the partial oxygen pressure which leads to 50% saturation.

The alpha-like globin genes of hemoglobin are clustered together on chromosome 16 and include genes encoding the embryonic zeta globin chain and the adult alpha globin chain, present in both the fetus and newborn. The beta-like globin genes reside on chromosome 11 and include genes encoding the embryonic epsilon-globin chain, the fetal gamma-globin chain, and the adult delta-globin and adult beta-globin chains. Two types of gamma globin chains have been identified, $^G$gamma and $^A$gamma, which differ by the presence of a single glycine of alanine residue, respectively, at amino acid 135 (Scroeder et al., 1968, Proc. Natl. Acad. Sci. U.S.A 60: 537–544). The gamma chain has been found to contain a polymorphic site at position 75, which also can be occupied either by isoleucine or threonine. A variety of hemoglobins may be formed (reviewed in Kutlar et al., 1989, Hemoglobin 13:671–683 and Honig and Adams, Human Hemoglobin Genetics, Springer Verlag, N.Y. pp, 29–33). Examples of hemoglobins (Hb) include hemoglobin A (HbA-alpha$_2$beta$_2$), HbA$_2$ (alpha$_2$delta$_2$), HbF (alpha$_2$gamma$_2$), Hb Barts (gamma$_4$), HbH (beta$_4$), and Hb Portland I (zeta$_2$gamma$_2$), Hb Portland II (zeta$_2$beta$_2$), Hb Portland III (zeta$_2$delta$_2$) Hb Gower I (zeta$_2$epsilon$_2$), and Hb Gower II (alpha$_2$epsilon$_2$).

There are obstacles however to using native hemoglobin as a blood substitute. Firstly, large dosages are required (Walder, 1988, Biotech '88, San Francisco, Nov. 14–16, 1988). A single unit (450 ml) of a 10% hemoglobin solution contains 45 g of protein. It is estimated that ten million units of blood are used in the U.S. per year. Therefore, the production of 450,000 kg of hemoglobin per year would be required. Secondly, it is important to obtain hemoglobin that is free from infectious agents and toxic substances. Thirdly, although hemoglobin is normally a tetramer of 64,000 molecular weight, it can dissociate to form alpha-beta dimers. The dimers are rapidly cleared by the kidneys and the residence time is much too short for cell-free hemoglobin to be useful as a blood substitute. Fourthly, cell-free hemoglobin has too high an oxygen affinity to effectively release oxygen to the tissue due to the absence of 2,3-diphosphoglycerate (2,3DPG). Efforts to restore 2,3-

DPG have been unsuccessful since 2,3-DPG is rapidly eliminated from the circulation.

CHEMICAL MODIFICATION OF HEMOGLOBIN

One approach that has been taken to circumvent the problem of dissociation of the hemoglobin tetramer to a dimer has been to chemically modify the hemoglobin by either intramolecular or intermolecular crosslinking. Examples of such modification include crosslinking with polyalkylene glycol (Iwashita, U.S. Pat. Nos. 4,412,989 and 4,301,144), with polyalkylene oxide (Iwasake, U.S. Pat. No. 4,607,417); with a polysaccharide (Nicolau, U.S. Pat. Nos. 4,321,259 and 4,473,563); with inositol phosphate (Wong, U.S. Pat. Nos. 4,710,488 and 4,650,786); with a bifunctional crosslinking agent (Morris et al., U.S. Pat. No. 4,061,736); with insulin (Ajisaka, U.S. Pat. No. 4,377,512); with a dialdehyde (Bonhard et al., U.S. Pat. No. 4,777,444); and with a crosslinking agent so that the hemoglobin composition is intramolecularly crosslinked between lys 99 alpha$_1$ and lys 99 alpha$_2$ (Walder, U.S. Pat. No. 4,598,064).

Another approach has involved the polymerization of hemoglobin to produce a polyhemoglobin. Polyhemoglobin has been found to have a longer circulation in blood than a hemoglobin tetramer. Polyhemoglobins have been obtained by crosslinking hemoglobin with glutaraldehyde (PCT Application Publication No. WO 88/03408; and Keipert et al., 1982, Int. J. Art. Org. 5:383–385).

Hemoglobin has also been chemically modified to decrease the oxygen affinity of isolated hemoglobin. One approach has involved polymerization with pyridoxal phosphate (Sehgal et al., 1984, Surgery, 95:433–438). A variation of the approach involving polymerization with pyridoxal phosphate has been disclosed and comprises reacting the hemoglobin with a stabilizing agent and then subsequently reacting the stabilized hemoglobin with pyridoxal phosphate (European Patent Application Publication No. 361,720, published Apr. 4, 1990; Tye, U.S. Pat. No. 4,529,719; and Maffuid et al., 1983, Surg. Forum 34:5–7). Another approach has involved the use of reagents that mimic 2,3-DPG (Bucci et al., U.S. Pat. No. 4,584,130; and Shimizu and Bucci, 1974, Biochemistry 13:809–814). Although these compounds do lower the oxygen affinity to hemoglobin, the affinity is still relatively high.

In another approach, hemoglobin has been crosslinked intramolecularly with periodate-oxidized ATP (o-ATP) and intermolecularly with periodate-oxidized adenosine (o-adenosine), and combined with reduced glutathione (GSH) (PCT Application Publication No. WO 91/09615).

SUMMARY OF THE INVENTION

The invention is directed to a stroma-free tetrameric mammalian hemoglobin having an affinity for oxygen which is lower than that of non-crosslinked hemoglobin A, and which is produced by a method comprising crosslinking with benzenepentacarboxylate, in which the crosslinking is carried out by a method comprising the step of activating at least two carboxylate groups of the benzenepentacarboxylate with an activating agent prior to reaction with the hemoglobin. The invention also provides for methods for preparation of such hemoglobin. An "activating agent" as defined herein is an agent that activates the carboxylate group so that the benzenecarboxylate may covalently attach to a hemoglobin's amino groups. Thus covalent bonding will occur, in addition to the expected salt bridge formation with 1-beta-valine, 143-beta histidine and 82-beta lysine residues. In a preferred embodiment, the benzenepentacarboxylate is activated at about two to three carboxylate groups on the benzenepentacarboxylate with a carbodimide. Crosslinked stroma-free hemoglobin produced by methods of the present invention may be used as a hemoglobin based oxygen carrier, specifically for example in applications requiring physiological oxygen carriers such as in blood substitute solutions, or as in a plasma expander.

DEFINITIONS

BPC: benzenepentacarboxylate
EDC: 1-ethyl-3-(-3-dimethyl-aminopropyl)carbodiimide
Hb: hemoglobin
HPLC: high pressure liquid chromatography
IHP: inositol hexaphosphate
Ret. Time: retention time
SDS: sodium dodecyl sulfate

BRIEF DESCRIPTION OF THE FIGURES

FIG. 4B shows a compilation of the reaction conditions used.

DETAILED DESCRIPTION OF THE INVENTION

Figure 1A:
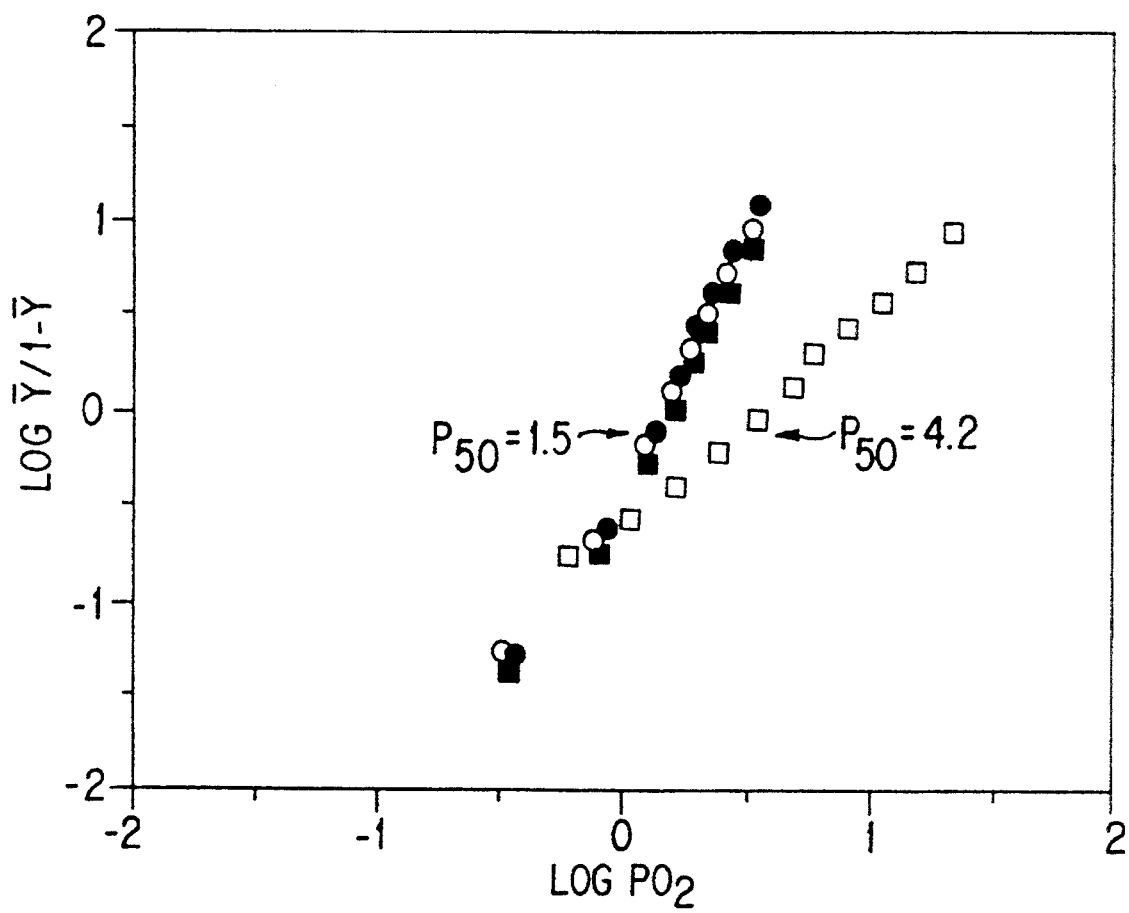
FIG. 1A shows the Hill Plot of O$_2$ binding in 50 mM Bis-Tris, pH 7.0 at 20° C. Legend for Hill Plot: ●-HbA; ○-HbA+50 fold EDC , □-HbA+200 fold BPC, dialyzed; ■-HbA+200 fold BPC, dialyzed and followed by 50 fold EDC.

The invention is directed to a stroma-free tetrameric mammalian hemoglobin having an affinity for oxygen which is lower than that of non-crosslinked hemoglobin A, and which is produced by a method comprising crosslinking with benzenepentacarboxylate in which at least two carboxylate groups are activated with an activating agent. The invention also provides methods for preparation of such hemoglobin. The mammalian hemoglobin may be for example, any human hemoglobin, including but not limited to HbA (alpha$_2$beta$_2$), HbA$_2$ (alpha$_2$delta$_2$), HbF (alpha$_2$gamma$_2$), Hb Barts (gamma$_4$), HbH (beta$_4$), and Hb Portland I (zeta$_2$gamma$_2$), Hb Portland II (zeta$_2$beta$_2$), Hb Portland III (zeta$_2$delta$_2$) Hb Gower I (zeta$_2$epsilon$_2$), and Hb Gower II (alpha$_2$epsilon$_2$); as well as any other animal hemoglobin, e.g. bovine or porcine hemoglobin. The activated benzenepentacarboxylate crosslinked hemoglobin may be used as a hemoglobin-based oxygen carrier, specifically for example in applications requiring physiological oxygen carriers such as in blood substitute solutions, or as in a plasma expander.

PREPARATION OF BENZENEPENTACARBOXYLATE-CROSS-LINKED LOW OXYGEN AFFINITY HEMOGLOBIN

Three steps are involved in the preparation of a stroma-free tetrameric mammalian hemoglobin having an affinity for oxygen which is lower than that of non-crosslinked hemoglobin A, and which is crosslinked with benzenepentacarboxylate in which at least two carboxylate groups are activated with an activating agent:

(a) obtaining a composition comprising hemoglobin;
(b) crosslinking the isolated hemoglobin with benzenepentacarboxylate, in which at least two carboxylate groups of the benzenepentacarboxylate are activated with an activating agent prior to the crosslinking; and
(c) recovering of the crosslinked hemoglobin.

OBTAINING HEMOGLOBIN

The starting material, unmodified hemoglobin, may be obtained using procedures known in the art (see for example PCT Application Publication No. WO 88/03408, published May 19, 1988; U.S. Pat. No. 4,001,401; Feola et al., 1983, Surgery Gynecology and Obstetrics 157:399-408; De Venuto et al., 1979, Surgery Gynecology and Obstetrics 149:417-436). For example, unmodified stroma-free hemoglobin may be obtained as follows: (a) obtaining whole blood; (b) separating red blood cells from other components of whole blood; (c) isolating the hemoglobin from the erythrocytes; and (d) separating the hemoglobin from stroma and other impurities.

Stroma-free hemoglobin is prepared starting with erythrocytes in freshly drawn, outdated, or frozen packed cells or whole blood. The blood should be drawn in a sterile fashion into containers with sufficient anticoagulant activity to prevent clot formation.

In one embodiment, the erythrocytes are washed in a saline solution and centrifuged to separate red blood cells from white blood cells and to additionally remove free proteins (Feola et al., 1983, Surgery Gynecology and Obstetrics 157:399-408). In another embodiment, the red cells may be separated from other erythrocytes by passing through a semi-continuous type centrifuge as described in PCT Application Publication No. WO 88/03408, published May 19, 1988.

Hemoglobin may be isolated in one embodiment by diluting the red blood cell solution in water or an organic solvent at 2°-10° C. to separate the hemoglobin in red blood cells from all cell debris (PCT Application Publication No. WO 88/03408, published May 19, 1988; U.S. Pat. No. 4,001,401; Feola et al., 1983, Surgery Gynecology and Obstetrics 157:399-408). In another embodiment, the hemoglobin is precipitated as a zinc complex by the addition of a zinc salt to a hemoglobin solution (De Venuto et al., 1979, Surgery Gynecology and Obstetrics 149:417-436).

The isolated hemoglobin may in one embodiment be purified by ultrafiltration through for example a 0.5 filter which retains the cellular components and passes the hemoglobin.

Hemoglobin may also be obtained through other procedures known in the art. For example, bacterial strains (see for example Nagai and Hoffman, U.S. Pat. No. 5,028,588, issued Jul. 2, 1991) or yeast (see for example PCT Application Publication No. WO90/13645, published Nov. 15, 1990), or other eukaryotic organisms may be engineered to produce hemoglobin by recombinant DNA techniques.

CROSSLINKING THE ISOLATED HEMOGLOBIN WITH ACTIVATED BENZENEPENTACARBOXYLATE

In a preferred embodiment, the hemoglobin is deoxygenated. Deoxygenation may be accomplished by extensively treating the hemoglobin prior to crosslinking with inert gases such as nitrogen, argon, or other inert gases. Alternatively, or in combination with inert gases, deoxygenation may be achieved by treating the hemoglobin with dithionite or other conventional reducing agents, such as ferrous citrate.

The benzenepentacarboxylate in a preferred embodiment, is activated before it is reacted with the hemoglobin. Activating agents include but are not limited to a carbodiimide or a thionyl chloride. In a preferred embodiment, the activating agent is 1-ethyl-3-(-3-dimethylaminopropyl)-carbodiimide. The activation of benzenepentacarboxylate with the activating agent can occur at a temperature of from about 15° C. to about 35° C., preferably from about 20° C. to about 30° C. The pH of the reaction can vary from about 6.5 to about 7.5, preferably at about 7, typically having an ionic strength of 0.01 molar Tris buffer in a molar salt solution up to a concentration of about 0.2 molar, preferably 0.05 molar. The ratio of benzenepentacarboxylate to activating agent should be from about preferably 2 to 3. The time for the reaction will vary, but can be up to 10 minutes for a sufficient activation of benzenecarboxylate to have occurred. In a preferred embodiment, from two to three carboxylate groups on benzenepentacarboxylate are activated.

The reaction of hemoglobin with the activated benzenepentacarboxylate can occur at a temperature of from about 15° C. to about 35° C., preferably from about 20° C. to about 30° C. The pH of the reaction can vary from about 6.0 to about 8.0, typically having an ionic strength of 0.01 molar Tris or bis-Tris buffer in a molar salt solution up to a concentration of about 0.2 molar, preferably 0.05 molar. If the reaction is carried out in Tris buffer, the pH is preferably about 6.0; if the reaction is carried out in bis-Tris buffer, the pH is about 8.0. The ratio of hemoglobin to activated benzenecarboxylate can be from about 1:20 to about 1:5, preferably 1:12 to about 1:8. The time for the reaction will vary, but can be up to 4 hrs. for a sufficient crosslinking of activated benzenepentacarboxylate to hemoglobin to have occurred. In a preferred embodiment, catalase (preferably 50 μl of 1 mg/ml solution) and/or EDTA (preferably 1 mM) are also added.

RECOVERY OF ACTIVATED BENZENEPENTACARBOXYLATE-CROSS-LINKED HEMOGLOBIN

The activated benzenepentacarboxylate-crosslinked hemoglobin may be isolated and purified using standard methods known in the art including but not limited to chromatography (e.g., ion exchange, affinity, and sizing column chromatography), centrifugation, differential solubility, or by any other standard technique for the purification of proteins. The chromatographic procedure employed may for example be high pressure liquid chromatography, fast pressure liquid chromatography, or ordinary column chromatography.

In a preferred embodiment, the $P_{50}$ of the purified activated benzenepentacarboxylate hemoglobin crosslinked by use of activated benzenepentacarboxylate is at least twice as high as hemoglobin A when measured under substantially the same conditions. The $P_{50}$ is defined as the partial pressure of $O_2$ required to cause 50% saturation of $O_2$ binding sites, and is an indication of oxygen affinity. The oxygen affinity of the purified hemoglobin produced by crosslinking with activated benzenepentacarboxylate may be determined using methods known in the art. These include but are not limited to tonometry, where bound oxygen is measured by a direct chemical reaction that gives moles of expelled gas (reviewed in Gill, Methods in Enzymology vol. 76, E. Antonini, L. Rossi-Bernardi, and E. Chancone, eds., Academic Press, NY (1981), pp. 427–439); a thin layer optical method where a thin layer of hemoglobin solution is exposed to oxygen at various partial pressures, while the oxygen saturation of the sample is monitored spectrophotometrically (reviewed in Gill, in Methods in Enzymology vol. 76, E. Antonini, L. Rossi-Bernardi, and E. Chancone, eds., Academic Press, NY (1981), pp. 427–438 and Lapennas et al., in Methods in Enzymology vol 76, E. Antonini, L. Rossi-Bernardi, and E. Chancone, eds., Academic Press, NY (1981), pp. 449–469); and a dynamic method where the partial pressure of oxygen, p, is changed continuously but slowly enough to maintain the equilibrium at any moment, and p and the fractional oxygen saturation of hemoglobin, Y are determined and recorded continuously (reviewed in Imai, in Methods in Enzymology vol. 76, E. Antonini, L. Rossi-Bernardi, and E. Chancone, eds., Academic Press, NY (1981), pp. 438–449).

USES FOR ACTIVATED BENZENEPENTACARBOXYLATE-CROSS-LINKED LOW OXYGEN AFFINITY HEMOGLOBIN

The hemoglobin compositions of the present invention may be used as blood substitutes or as a blood plasma expander, in a pharmaceutical composition with an acceptable carrier, and with other plasma expanders, or in any application where a physiological oxygen carrier is needed. The pharmaceutical carriers may be such physiologically compatible buffers as Hank's or Ringer's solution, physiological saline, a mixture consisting of saline and glucose, and heparinized sodium-citrate-citrate acid-dextrose solution. The hemoglobin produced by the methods of the present invention can be mixed with colloidal-like plasma substitutes and plasma expanders such as linear polysaccharides (e.g. dextran), hydroxyethyl starch, balanced fluid gelatin, and other plasma proteins. Additionally, the hemoglobin may be mixed with water soluble, physiologically acceptable, polymeric plasma substitutes, examples of which include polyvinyl alcohol, poly(ethylene oxide), polyvinylpyrrolidone, and ethylene oxide-polypropylene glycol condensates. Techniques and formulations for administering the compositions comprising the hemoglobin generally may be found in Remington's Pharmaceutical Sciences, Meade Publishing Col., Easton, Pa., latest edition.

The following examples are presented by way of illustration not by way of limitation.

EXAMPLE: CARBODIIMIDE-MEDIATED COUPLING OF BENZENEPENTACARBOXYLATE (BPC) TO HUMAN HEMOGLOBIN

Benzenepentacarboxylate (BPC) binds reversibly to hemoglobin's 2,3-diphosphoglycerate-binding site and decreases the protein's affinity for oxygen (Shimizu and Bucci, 1974, Biochemistry 13: 809–814). Specifically the carboxyl groups of benzenepentacarboxylate (BPC) form salt bridges with 1-beta-valine, 143-beta histidine and 82-beta lysine residues. In the example described herein, the carboxylate groups of BPC were activated with EDC, so that BPC can covalently attach to the amino groups on the hemoglobin resulting in modified hemoglobin that is stable and has a significantly lower oxygen affinity than BPC-modified hemoglobin generated without activation.

PREPARATION OF HEMOGLOBIN FROM WHOLE BLOOD

The following procedure was used in the preparation of hemoglobin from whole blood. The procedure was generally carried out at 0° C. The blood was centrifuged at 2000 g for five minutes. The supernatant was drawn off by aspiration, using a Pasteur pipette.

The red blood cells were washed three times with 5–10 volumes of 0.8% sodium chloride. The cells were lysed with four volumes of cold deionized water, stirred with a glass rod or vortexed, during the addition of the water. After lysis, the hemolysate was greatly stirred in a beaker or flask immersed on crushed ice for fifteen minutes. Unlysed cells and stroma were removed by high speed centrifugation. Subsequently, 0.2 volumes of saturated ammonium sulphate to the clear supernatant (saturated at 4° C.).

After allowing hemoglobin to stand for 10 minutes with no stirring, the solution was centrifuged at 27,000 g in the SS-34 rotor of the Sorvall centrifuge for 30 minutes. The hemolysate (supernatant) was dialyzed versus 2-3 changes of cold deionized water for +24 hours (50 volumes excess of water over hemolysate).

The dialyzed hemolysate was centrifuged at 27,000 g on the SS-34 rotor rotor, for 10 minutes. At this stage, the dialyzed hemolysate was more or less salt free, but some DPG or other organic anionic effectors of hemoglobin was still attached to the hemoglobin. The DPG and anionic effectors were removed on an amberlite MB-3 column. Volumes of 100-200 ml of hemolysate were passed over the MB-3 column, equilibrated with deionized water.

PREPARATION OF LOW-OXYGEN AFFINITY HEMOGLOBIN BY MODIFICATION WITH EDC-ACTIVATED BPC

REMOVAL OF EXCESS BPC BY DIALYSIS OR BY DESALTING ON SEPHADEX G-25

Figure 1B:
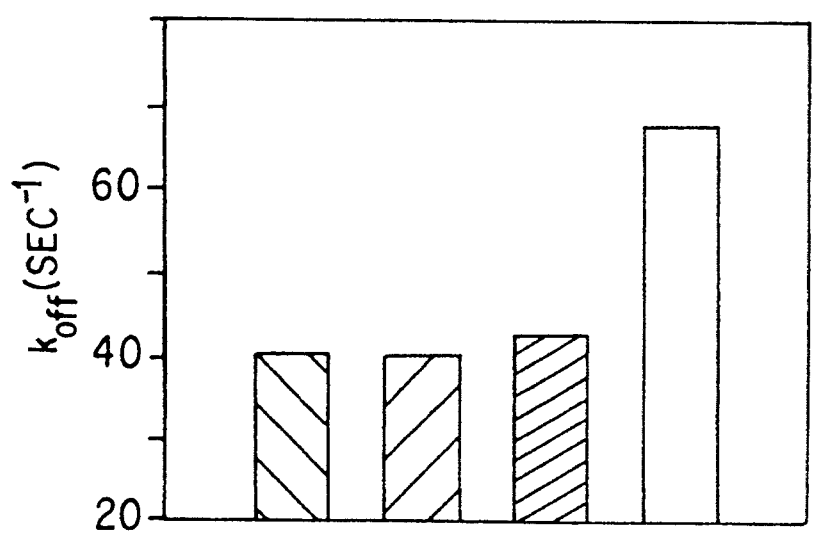
FIG. 1B shows O$_2$ dissociation constants. Legend for FIG. 1B: ⊠-HbA; ▨-Hba+50 fold EDC; ▧-Hba+200 fold BPC, dialyzed; □-HbA+200 fold BPC, dialyzed and followed by 50 fold EDC.

HbA was incubated at pH 7 for 5 hours with a 200 fold excess of BPC, followed by dialysis for 16 hours. The BPC-hemoglobin was incubated with a 50-fold excess of BPC for 5 hours, dialyzed for 4 hours against 50 mM Bis-Tris, pH 7.0, followed by 16 hours against 3 mM Bis-Tris, pH 7.0. The sample was chromatographed twice on a mixed bed ion-exchange column and then made up to 50 mM Bis-Tris pH 7.0. The results of oxygen equilibrium and oxygen dissociation experiments with these samples are shown in FIGS. 1A-1B tabulated in Table I.

TABLE I

|            | $P_{50}$ | $N_{50}$ | $O_2$ off rate (sec$^{-1}$) |
|------------|----------|----------|------------------------------|
| HbA        | 1.56     | 2.8      | 40                           |
| HbA + EDC  | 1.55     | 2.7      | 40                           |
| HbA + BPC  | 1.66     | 2.9      | 43                           |
| HbA + BPC + EDC | 4.17 | 1.2      | 67                           |

The $P_{50}$ was determined by tonometry (Riggs and Wolbach, 1956, J. Gen. Physiol. 39: 585-605). Specifically, a hemoglobin solution was placed in a gas-tight vessel which has an attached spectrophotometer cell. The solution was deoxygenated by a series of repeated vacuum evacuations followed by nitrogen purges. After the deoxygenated state was obtained, a "deoxy" spectrum was obtained. Next, a series of metered oxygen additions were made with a spectrum taken after each addition yielding a set of curves from which can be calculated (using established extinction coefficients) the degree of saturation of the heme sites with oxygen as a function of the oxygen partial pressure.

The $O_2$ off rate is the rate of dissociation of $O_2$ from oxyhemoglobin and was determined by stopped-flow spectrophotometry (Olson in Methods in Enzymology, vol. 76, E. Antonini, L. Rossi-Bernardi, and E. Chancone, eds., Academic Press, N.Y. (1981), pp. 438-449). Specifically, a solution of oxyhemoglobin was mixed rapidly with a solution of sodium dithionite and the absorbance of the reaction mix was monitored at a wavelength which allows the discrimination of oxyhemoglobin and deoxyhemoglobin (473. 5 nm). Sodium dithionite rapidly scavenges the free oxygen in the solution and oxygen which becomes available from the thermodynamic dissociation of oxyhemoglobin into deoxyhemoglobin and oxygen. The rate of absorbance change measured is thus proportional to the first order dissociation of oxyhemoglobin into deoxyhemoglobin and oxygen.

The hemoglobin samples treated with BPC and EDC as shown in Table I have a much lower oxygen affinity than samples reacted with BPC and EDC alone. The lower oxygen affinity finds its kinetic origin in a increased rate of oxygen dissociation.

The same experiment carried out with DPG instead of BPC gives Hb with normal oxygen binding properties: DPG cannot be crosslinked into the beta-chain cavity. BPG-modified Hb moves much faster on cellulose acetate than HbA, and is much more spread out (not a single peak).

ACTIVATION OF BPC WITH SUBSTOICHIOMETRIC AMOUNTS OF EDC PRIOR TO THE ADDITION OF HEMOGLOBIN

Figure 2A:
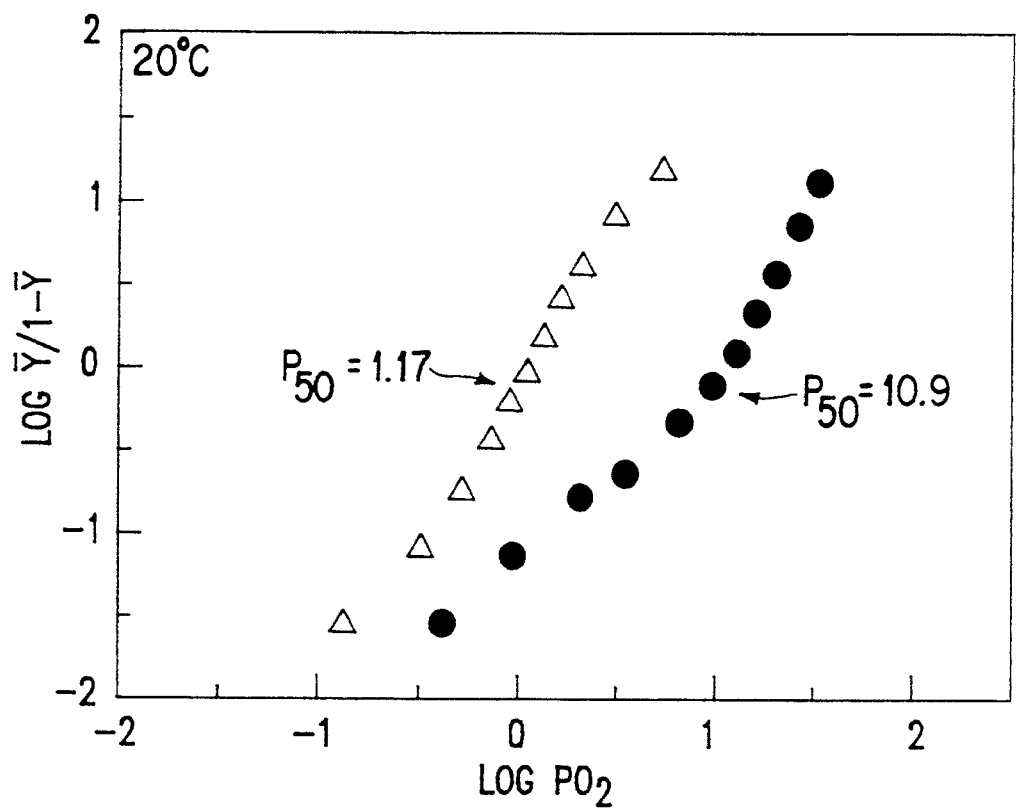
FIGS. 2A–2B show the Hill Plot of O$_2$ binding in 50 mM Bis-Tris, pH 7.0 at 20° C. ●-HbA incubated with 10 fold BPC/EDC (½); ▲-HbA incubated with 10 fold BPC. All samples were "stripped" on Sephadex G-25 and Amberlite mixed-bed resin to remove non-covalently bound BPC.
Figure 2B:
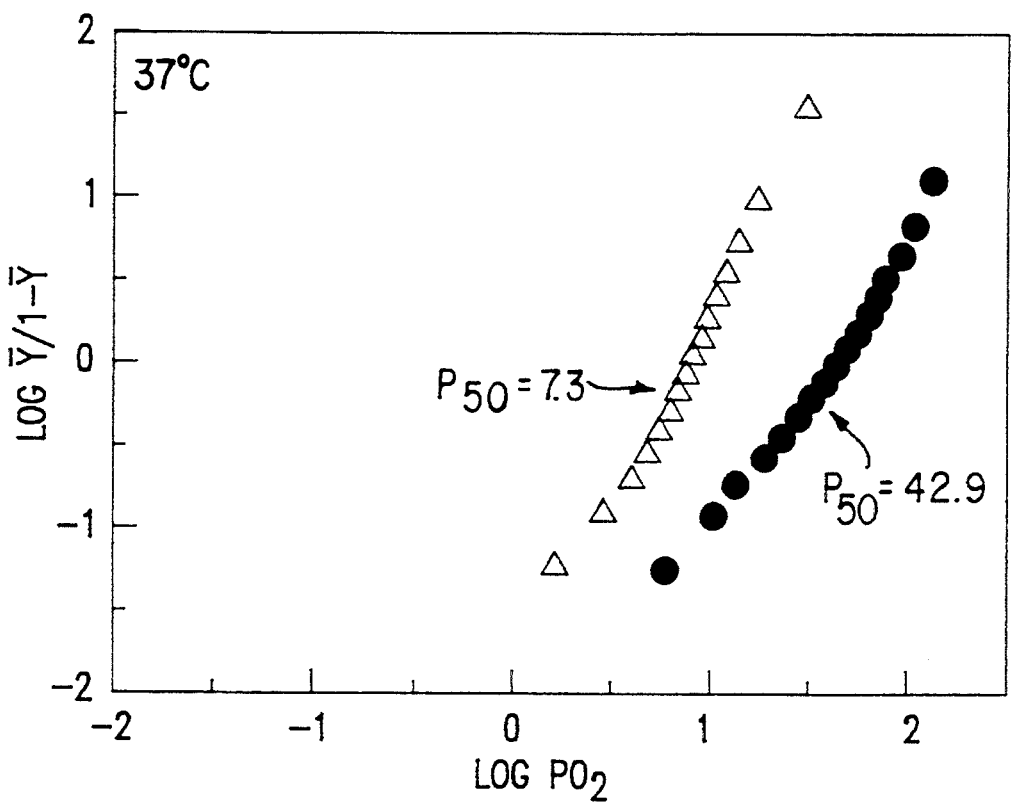

A BPC solution in deionized water adjusted to pH 8.0 is incubated with 3 fold EDC for 15 min. at room temperature (R.T.) and then added to HbA samples in 0.05M Tris-HCl, pH 8.0 at a concentration of 140 μM Hb (tetramer) in 2, 10, 50 and 200 fold excess. The final BPC concentration is 0.3 mM, 1.5 mM, 7.5 mM and 30 mM, respectively. The samples are incubated for 4 hours at R.T. and then freed from excess BPC by filtration through a PD-10 Sephadex G-25 column equilibrated with 3 mM Bis-Tris, pH 7.0 and twice stripped over an Amberlite mixed bed resin equilibrated with deionized water. The same procedure is followed for HbA samples incubated with 1.5 mM and 7.5 mM BPC not activated with EDC. Oxygen binding experiments are carried out in 50 mM Bis-Tris, pH 7.0. Some of the binding curves are shown in FIGS. 2A-2B, and the results are tabulated in Table II.

TABLE II

|                          | $P_{50}$ (mm Hg) | $N_{50}$ |
|--------------------------|------------------|----------|
| HbA + 333 μM BPC (EDC)   | 1.71             | 1.03     |
| HbA + 1.5 mM BPC (EDC)   | 10.88            | 1.63     |
|                          | 10.79            | 1.67     |
| HbA + 7.5 mM BPC (EDC)   | 10.86            | 1.49     |
|                          | 10.93            | 1.39     |
| HbA + 30 mM BPC (EDC)    | .53              | .76      |
| HbA + 1.5 mM BPC         | 1.17             | 2.52     |
| HbA + 7.5 mM BPC         | 1.01             | 1.95     |

The HbA samples incubated with 1.5 and 7.5 mM BPC (activated with EDC) give hemoglobin preparations with low oxygen affinity and cooperative oxygen binding. BPC not activated with EDC does not alter the oxygen binding properties of hemoglobin.

ACTIVATION OF BPC WITH EDC PRIOR TO ADDITION OF HbA

The oxygen binding of (1) Hb derivatives incubated with BPC followed by EDC is compared with (2) Hb derivatives incubated with EDC-activated BPC.

Figure 3:
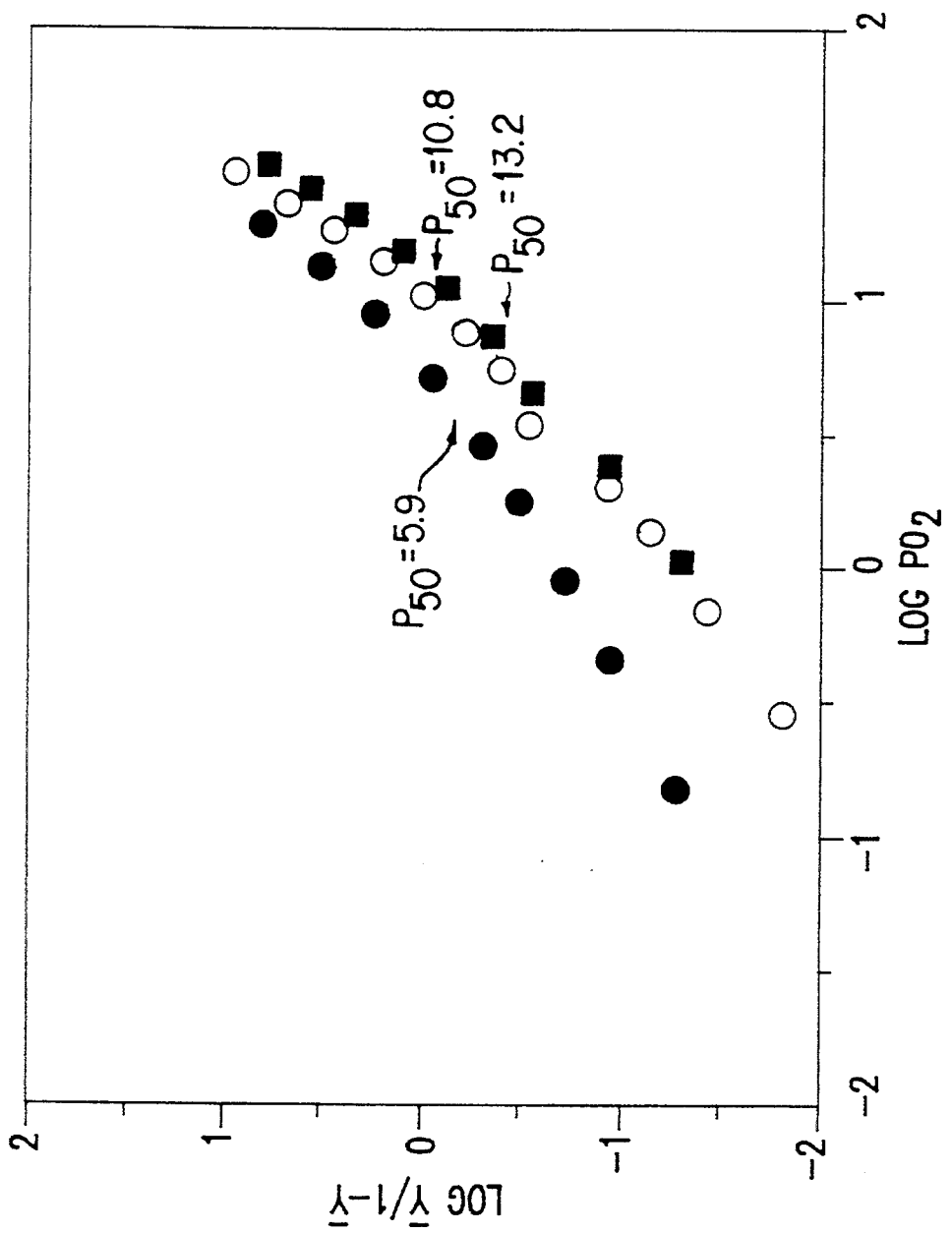
FIG. 3 shows the Hill Plot of O$_2$ binding in 50 mM Bis-Tris, pH 7.0 at 20° C. ●-HbA+10 fold BPC+3 fold EDC (oxy); ○-HbA+10 fold BPC/EDC (½) (oxy); ■-HbA+10 fold BPC/EDC (½) (deoxy).

HbA samples in 0.05M Tris-HCl pH 8.0 at a concentration of 150 μM Hb (tetramer) are incubated with a 10 (1.5 mM) and 50 (7.5 mM) fold excess BPC for 5 min. at R.T. A 3 fold excess EDC (4.5 mM and 22.5 mM EDC, respectively) was added and the samples were incubated for 4 hours at R.T. The samples were freed from excess BPC and EDC by chromatography on a mixed bed ion-exchange column. The same procedure is followed for HbA samples incubated with EDC only. Oxygen binding experiments are carried out in 50 mM Bis-Tris, pH 7.0. Some of the binding curves are shown in FIG. 3 and the results are compiled in Table III.

TABLE III

| | $P_{50}$ (mm Hg) | $N_{50}$ | pH |
|---|---|---|---|
| HbA + 1.5 mM BPC + 4.5 mM EDC | 5.86 | 1.24 | 7.02 |
| HbA + 7.5 mM BPC + 22.5 mM EDC | .37 | .81 | 7.02 |
| HbA + 4.5 mM EDC | 1.17 | 3.37 | 7.03 |
| HbA + 22.5 mM EDC | 1.00 | 1.99 | 7.02 |
| 1.5 mM BPC + 4.5 mM EDC + HbA | 10.79 | 1.57 | 7.03 |
| 7.5 mM BPC + 22.5 mM EDC + HbA | 10.93 | 1.39 | 7.04 |

From these results, it is evident that activation of BPC with EDC prior to addition of HbA constitutes a superior pathway for the preparation of low-oxygen affinity Hb derivatives. When EDC is added to the HbA/BPC solution the oxygen binding curve shows that the deoxy-asymptote of the Hill plot is shifted to the left (FIG. 3), indicating that reaction of EDC with HbA interferes with the formation of the T-state quaternary conformation.

ANALYSIS OF BPC-MODIFIED HEMOGLOBIN BY SIZE EXCLUSION HPLC AND SDS GEL ELECTROPHORESIS

HbA samples were deoxygenated gasometrically. Deoxy HbA samples at a concentration of 150 μM were incubated with different concentrations of BPC and activated with different concentrations of EDC as described in Section 6.3., supra.

50 FOLD EXCESS BPC OVER HEMOGLOBIN

Deoxy H samples were incubated with a 50 fold excess of activated BPC over hemoglobin for 4 hrs. at room temperature using BPC/EDC ratios of 2, 4, 5 and 10. The samples were subsequently analyzed by HPLC chromatography using a TSK 3000 SW ion exchange column Beckman and eluted with 0.05M Tris, pH 7.5. Table IV, infra shows the retention times of the peaks detected, as well as the relative amount (%) of material present in each peak.

TABLE IV

| BPC/EDC | Ret. Time | % | Ret. Time | % | Ret. Time | % | Ret. Time | % | $P_{50}$ |
|---|---|---|---|---|---|---|---|---|---|
| 2 | — | — | 6.4 | 13 | 7.0 | 65 | 7.43 | 23 | 9.0 |
| 4 | — | — | 6.3 | 37 | 6.8 | 63 | — | — | 6.5 |
| 5 | 6.1 | 45 | — | — | 6.7 | 50 | — | — | 5.0 |
| 10 | 6.0 | 52 | 6.4 | 46 | — | — | — | — | 4.9 |

Figure 4A:
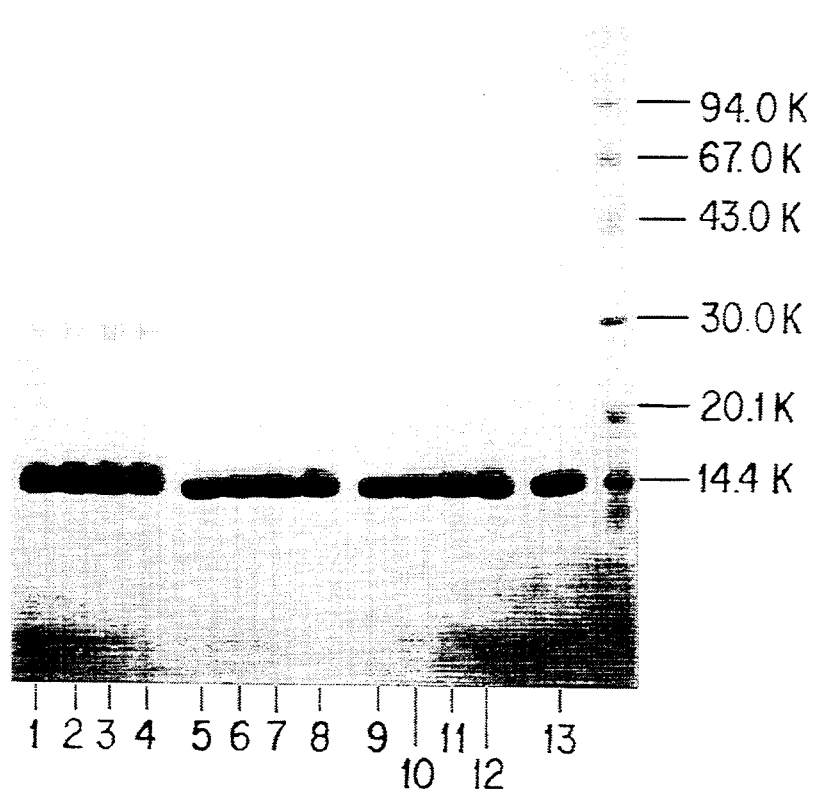
FIG. 4A shows SDS gel electrophoresis of HbA modified with 7.5 mM BPC (lanes 1–4); 3.0 mM BPC (lanes 5–8); and 1.5 mM (BPC) and EDC with BPC/EDC ratios of 1/0 (line 9); 1/1 (lanes 5 and 10); ½ (lanes 1, 6, and 11); ⅓ (lanes 7 and 12); ¼ (lane 2); 1/5 (lane 8); 1/6 (lane 3); 1/10 (lane 4). Lane 13 shows HbA, not modified.

Unmodified hemoglobin tetramers elute with a retention time of approximately 8.3 minutes. These tetramers dissociate upon dilution resulting in a shift of the retention time towards 9 minutes. The BPC-modified samples listed in Table IV, supra, do not dissociate upon dilution, and unmodified tetramers do not seem to be present. The decrease in retention time of hemoglobin after treatment with BPC/EDC may be due to an increase in molecular weight of hemoglobin due to intermolecular crosslinking of tetramers, or to interaction of the chemically modified protein with the column matrix. Discontinuous SDS gel electrophoresis (see Laemmli, 1971, Nature 277:680) using a 10–15% gradient gel, of samples reduced with beta-mercaptoethanol does shows an increase of crosslinked globin chains with increasing BPC/EDC ratios (FIGS. 4A–4B; lanes 1 and 4). The SDS gels also demonstrate the presence of modified, uncrosslinked globin chains, which move close to the unmodified alpha and beta chains.

20 FOLD EXCESS BPC OVER HEMOGLOBIN

Deoxy HbA samples were incubated with a 20 fold excess of activated BPC over hemoglobin for 4 hrs. at room temperature using BPC/EDC ratios of 1, 2, 3 and 5. The samples were subsequently analyzed by HPLC chromatography using a TSK 3000 SW ion exchange column (Beckman) and eluted with 0.05M Tris, pH 7.5. Table V, infra shows the retention times of the peaks detected, as well as the relative amount (%) of material present in each peak.

TABLE V

| BPC/EDC | Ret. Time | % | Ret. Time | % | Ret. Time | % | Ret. Time | % | $P_{50}$ |
|---|---|---|---|---|---|---|---|---|---|
| 1 | — | — | — | — | 7.7 | 30 | 8.47 | 70 | 13.9 |
| 2 | — | — | 7.2 | 7 | 7.6 | 47 | 8.35 | 43 | 15.1 |
| 3 | — | — | 7.3 | 19 | 7.6 | 55 | 8.33 | 26 | 14.6 |
| 5 | 6.5 | 11 | 7.1 | 53 | 7.5 | 28 | 8.53 | 6 | 9.4 |

When excess BPC over hemoglobin is reduced from 50- to 20-fold, a peak in the HPLC elution profile is observed, which elutes with the same retention time as that of unmodified tetramers. The retention time of this peak shifts when the hemoglobin solution is diluted. The peaks eluting around 7.6 and 7.2 minutes do not shift upon dilution. Increasing the EDC/BPC ratio from 1 to 3 decreases the fraction of labile tetramers from 70% to 26%. Yet, the $P_{50}$ under those conditions remains the same. BPC-modification of hemoglobin apparently leads to at least two important but distant modifications. at BPC/EDC =1/1 the tetramers are modified in such a way that their oxygen affinity decreases. These tetramers still dissociated into dimers upon dilution. As will be shown below, and as we have shown before, the oxygen affinity of these samples is not affected by IHP. It seems, therefore, that the BPC molecules are covalently attached to the DPG (IHP)-binding site. Increasing the amount of EDC to activate BPC leads to additional modification of hemoglobin giving rise to derivatives that are stable towards dissociation. SDS gels (FIGS. 4A–4B, lanes 5 through 8) show increasing amounts of modified globin chains. Whether these represent modified beta and/or alpha chains needs to be determined. Only at the highest EDC/BPC ratio are dimers (32K) observed. This indicates that the peaks eluting at 7.6 and 7.2 minutes are not hemoglobin polymers. Apparently, in addition to acting as a molecular sieve, the TSK 3000 SW column acts as an ion-exchanger in the low ionic strength buffer (50 mM Tris, pH 7.5) used to elute the column.

10-FOLD EXCESS BPC OVER HEMOGLOBIN

Deoxy HbA samples were incubated with a 20 fold excess of activated BPC over hemoglobin for 4 hrs. at room temperature using BPC/EDC ratios of 1, 2, 3 and 5. The samples were subsequently analyzed by HPLC chromatography Table VI, infra shows the retention times of the peaks detected, as using a TSK 3000 SW ion exchange column (Beckman) and eluted with 0.05M Tris, pH 7.5, well as the relative amount (%) of material present in each peak.

TABLE VI

| BPC/EDC | Ret. Time | % | Ret. Time | % | $P_{50}$ | $P_{50}$ + IHP |
|---|---|---|---|---|---|---|
| 0 | | | 9.5 | 100 | 0.68 | 37.4 |
| 1 | 9.1 | 16 | 9.4 | 84 | 14.4 | 18.7 |
| 2 | 9.1 | 31 | 9.4 | 69 | 17.1 | 19.3 |
| 3 | 9.0 | 43 | 9.4 | 57 | 17.3 | 25.5 |

During the course of the experiments described in this section, a sudden change in the elution characteristics of the TSK 3000 SW column is evident. Hemoglobin is bound to the column and eluted as a very broad peak with a long trailing edge. Attempts to revive the column were unsuccessful. In order to obtain sharp hemoglobin peaks, the ionic strength of the elution buffer is raised by the addition of 0.1M NaCl. Hemoglobin tetramers now elute with a retention time of around 9.4 minutes. BPC-modification gives rise to a second hemoglobin derivative eluting around 9 minutes. The increase in this component, accompanied by a decrease in tetramers, does not change the oxygen affinity of the modified hemoglobin. The tetramers eluting at 9.4 minutes dissociate upon dilution. The 9 minute component seems to be stable. This observation again indicates the occurrence of two distinct modifications of hemoglobin, as discussed above. IHP has only a small effect on the oxygen affinity of the modified hemoglobin. SDS gels (FIGS. 4A–4B, lanes 9 through 12) of the mercaptoethanol-reduced samples show the presence of an additional band moving close to the alpha and beta chains.

In conclusion, we may say that the BPC modification was successful. Two functionally distinct modifications seem to occur. One that lowers the oxygen affinity of the hemoglobin tetramers, without affecting its stability, and a second that converts the hemoglobin tetramer into a stable non-dissociable tetramer.

SYNTHESIS OF HEMOGLOBIN MODIFIED WITH BPC/EDC IN THE PRESENCE OF CATALASE AND EDTA

Benzenepentacarboxylate (BPC) is preactivated with a two-fold excess of 1-ethyl-3-(-3-dimethyl-aminopropy)-carbodiimide (EDC) for five minutes at room temperature. The preactivated BPC is reacted with 10 ml of 600 μM of human hemoglobin in 50 mM Tris at pH 6.0 and in 50 mM bis-Tris at pH 8.0 in the presence of 1 mM EDTA and 38 μg of calatase for one hour at room temperature in a nitrogen atmosphere.

Catalase breaks down hydrogen peroxide and EDTA chelates metal ions at pH 6.0 and 8.0. The presence of catalase and EDTA prevent the occurrence of the Fenton reaction:

$Fe^2 + (Cu^1+) + H_2O_2 \rightarrow Fe^3 + (Cu^2+) + OH + OH$

The hydroxyl radical (OH) is primarily responsible for oxidative damage to macromolecules (protein, DNA, and cellular membranes). This treatment was found to reduce the formation of oxidized (met) hemoglobin produced by the modification.

The reacted mixture is dialyzed to 50 mM Tris, pH 8.0 overnight and the components are separated by ion exchange on a DEAE Sepharose column with a 0 to 0.3M NaCl gradient. (See FIG. 5).

CHARACTERIZATION OF BPC/EDC MODIFIED HEMOGLOBIN

Figure 6:
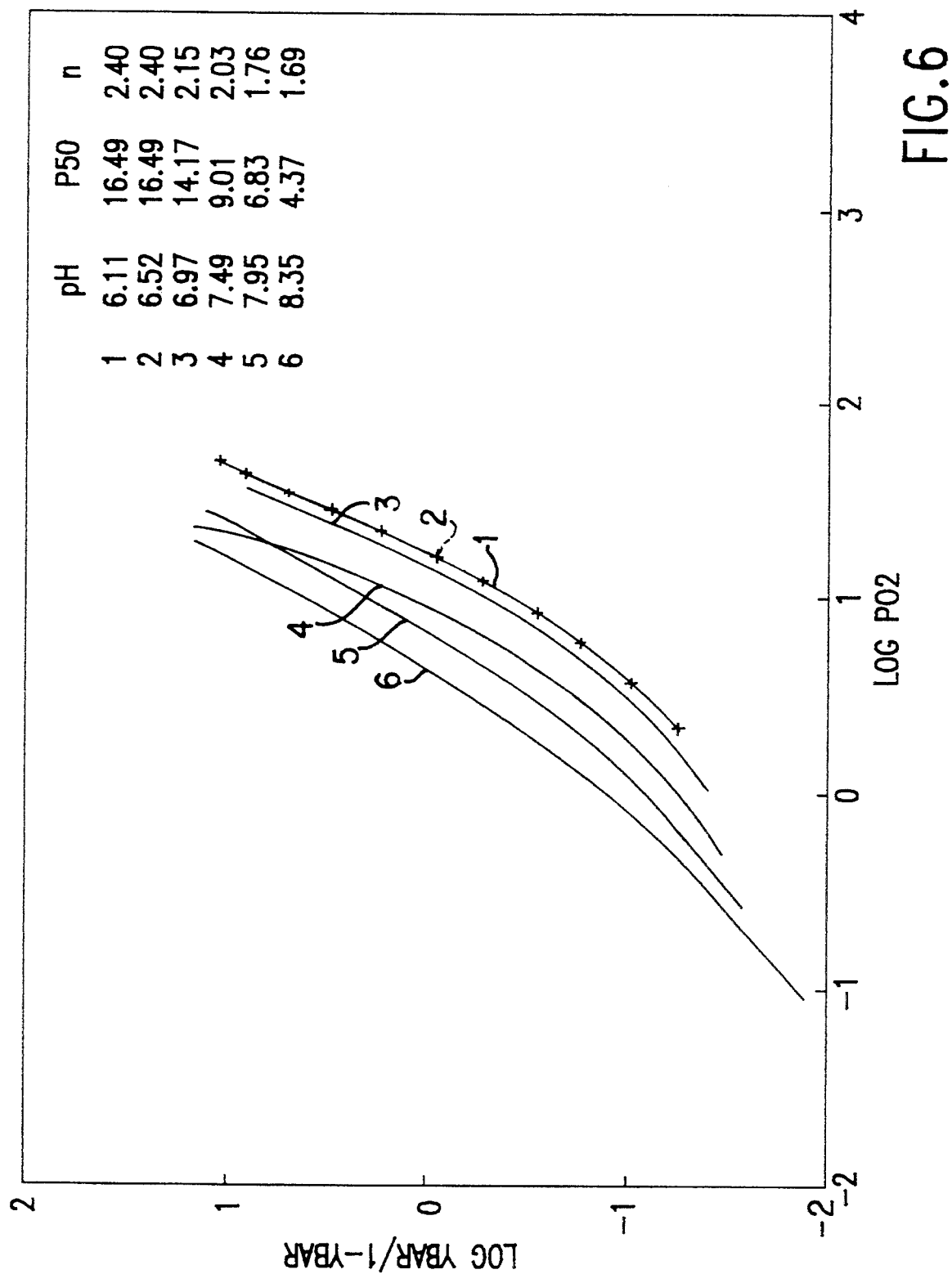
FIG. 6 shows a Hill plot of peak 2 at pHs 6.11–8.35 at 20° C.
Figure 7:
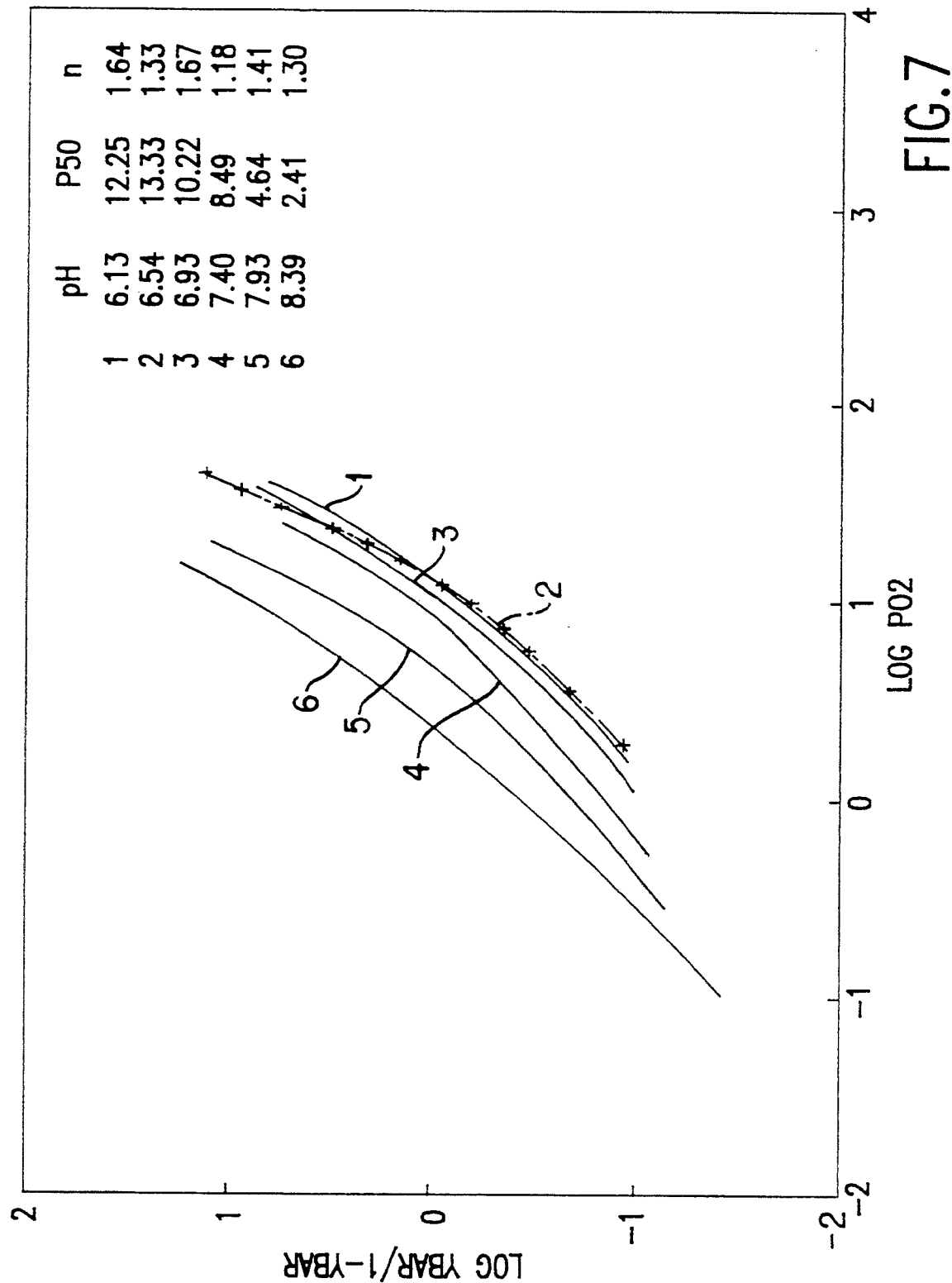
FIG. 7 shows a Hill plot of peak 3 at pHs 6.13–8.39 at 20° C.
Figure 8:
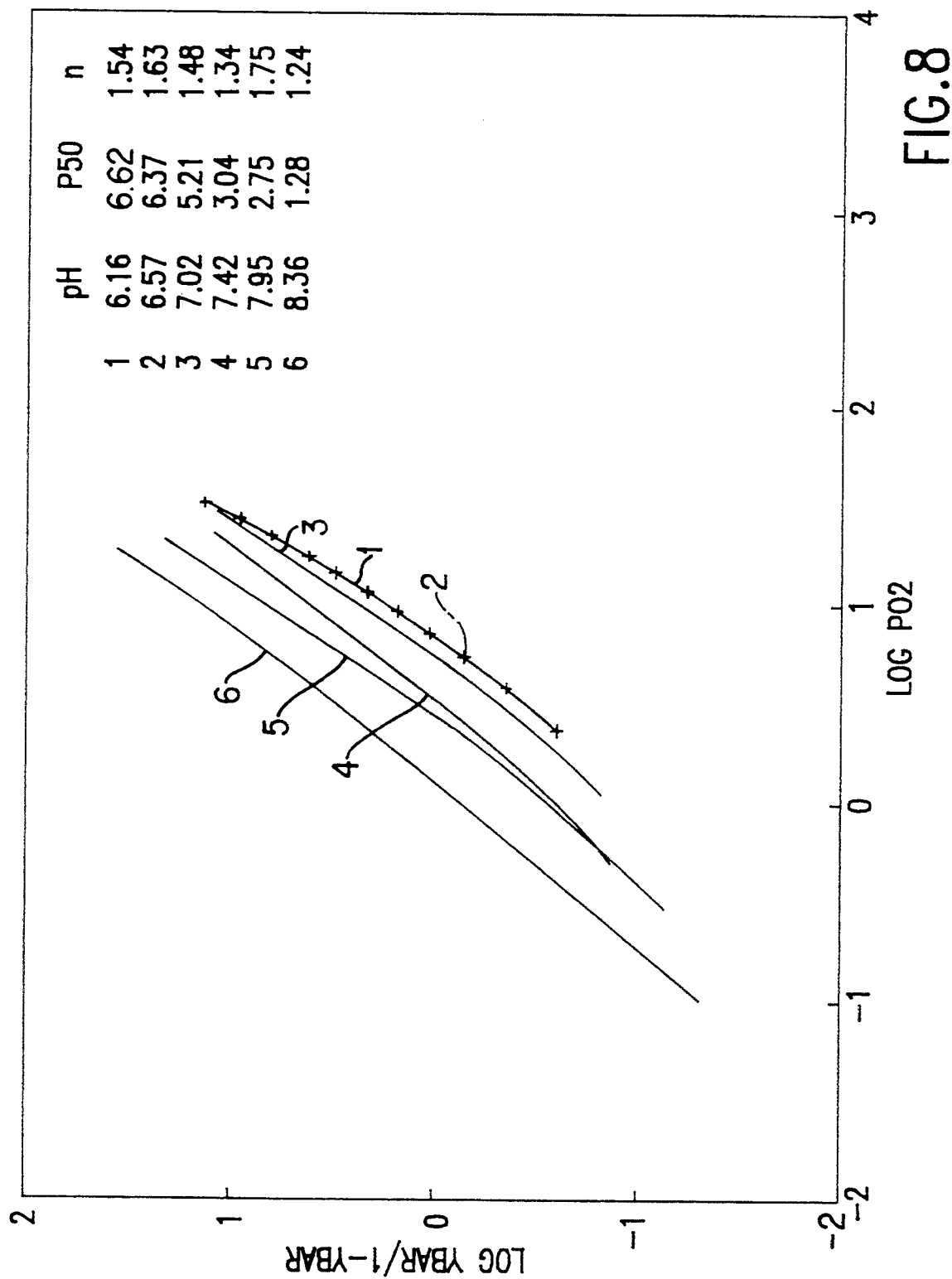
FIG. 8 shows a Hill plot of peak 4 at pHs 6.16–8.36 at 20° C.

Modified HbA, prepared at pH 8, can be separated into three components. Peak #1 is unreacted hemoglobin. Peaks #2 and #3 are reaction products. The reaction at pH 6 is more efficient: essentially no unreacted hemoglobin is present. It is also clear that the modified hemoglobin derivatives obtained at the two pH values occupy different positions in the ion-exchange profile, indicating that they represent chemically distinct species. The oxygen binding properties of the three Hb derivatives (called peak #2, #3 and #4) prepared at pH 6 were characterized as a function of pH. The Hill plots of oxygen binding at various pH values are shown in FIGS. 6, 7 and 8. The oxygen affinities and Hill coefficients are listed in Table VII:

TABLE VII

| PEAK # | pH | Log p50 | p50 | $N_{50}$ |
|---|---|---|---|---|
| 2 | 6.11 | 1.2171 | 16.41 | 2.40 |
| 2 | 6.52 | 1.2131 | 16.33 | 2.09 |
| 2 | 6.97 | 1.1513 | 14.17 | 2.15 |
| 2 | 7.49 | 0.9546 | 9.01 | 2.03 |
| 2 | 7.94 | 0.8344 | 6.83 | 1.76 |
| 2 | 8.35 | 0.6408 | 4.37 | 1.69 |
| 3 | 6.13 | 1.0880 | 12.25 | 1.64 |
| 3 | 6.54 | 1.1249 | 13.33 | 1.33 |
| 3 | 6.93 | 1.0093 | 10.22 | 1.67 |
| 3 | 7.40 | 1.9290 | 8.49 | 1.18 |
| 3 | 7.93 | 0.6661 | 4.64 | 1.41 |
| 3 | 8.39 | 0.3817 | 2.41 | 1.30 |
| 4 | 6.16 | 0.8207 | 6.62 | 1.54 |
| 4 | 6.57 | 0.8042 | 6.37 | 1.63 |
| 4 | 7.02 | 0.7168 | 5.21 | 1.48 |
| 4 | 7.42 | 0.4832 | 3.04 | 1.34 |
| 4 | 7.95 | 0.4401 | 2.75 | 1.75 |
| 4 | 8.36 | 0.1060 | 1.28 | 1.24 |

Figure 9:
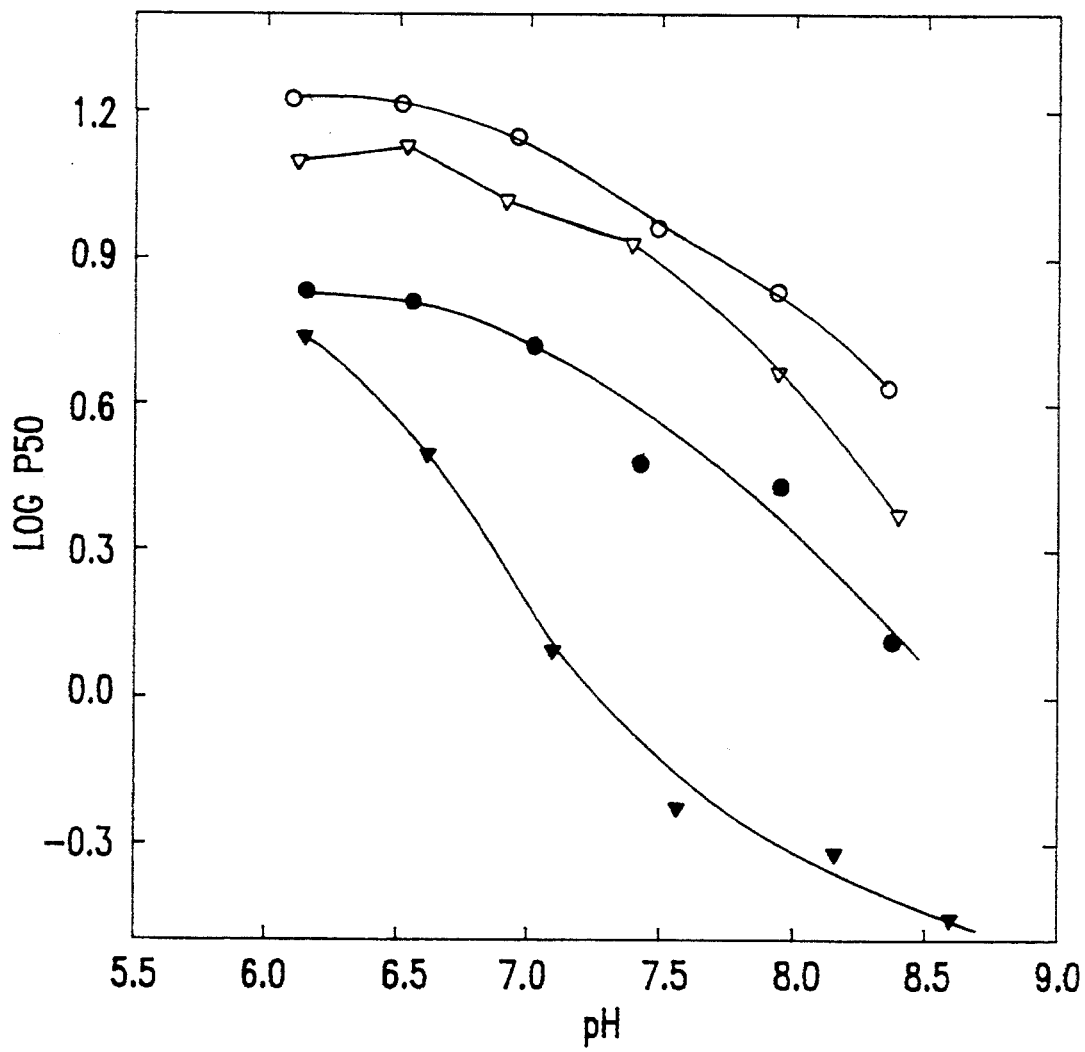
FIG. 9 shows a BPC/EDC modification Bohr effect curve of HbA derivatives prepared at pH 6, under N$_2$ in Tris and Bis/Tris buffers at 20° C. ○-peak #2; ▽-peak #3; ●-peak #4; and ▼-HbA$_0$.

FIG. 9 shows the Log $P_{50}$ values as a function of the pH. It is most striking that the alkaline Bohr effect (i.e. increase in oxygen affinity above pH 6 with pH) of all three modified hemoglobins is greatly reduced with respect to that of HbA, especially between pH 6 and pH 7. The same was observed for peaks #2 and #3 obtained after modification of HbA with BPC at pH 8. The macroscopically measured Bohr effect is a summation of the effects of changes in the pK values that occur upon changing the ligation state of the Hb molecule. Any group that changes its ionization constant between the deoxy and oxy forms of the Hb molecule participates in the Bohr effect. It is inappropriate to assume that all sites have pK changes that result in positive contributions to the macroscopically observed effect. The microscopic behavior of a specific group will be denied by its site-specific chemical and electrostatic environments, and its resulting microscopic behavior may oppose the macroscopic behavior seen for the Hb molecule. (Ho and Russu, 1987, Biochemistry 26: 6299–6305 and Busch et al., 1991, Biochemistry 30: 1865–1877). It is also well established that a major part of the alkaline Bohr effect is contributed by oxygen-linked ionization of the imidazole groups of the carboxyl-terminal histidines of the β chains and the α-amino groups of the α chains. A large fraction of the Bohr effect of Hb originates from the heterotropic interactions between HbA and anions. These effects can be explained as being due to a difference in the anion binding affinities between the deoxy and ligated states of HbA. β2H is in both deoxy and CO forms of HbA is a strong binding site for both inorganic phosphate and 2,3-DPG. Thus this residue plays an important role in the Bohr effect of HbA in the presence of inorganic and organic phosphate ions. The fact that benzenepentacarboxylate bound to HbA reduces Hb's Bohr effect strongly suggests that the

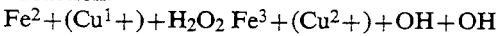

carboxy groups of BPC form salt bridges with one or more of the Bohr effect residues, thereby making their ionization more difficult.

Figure 10:
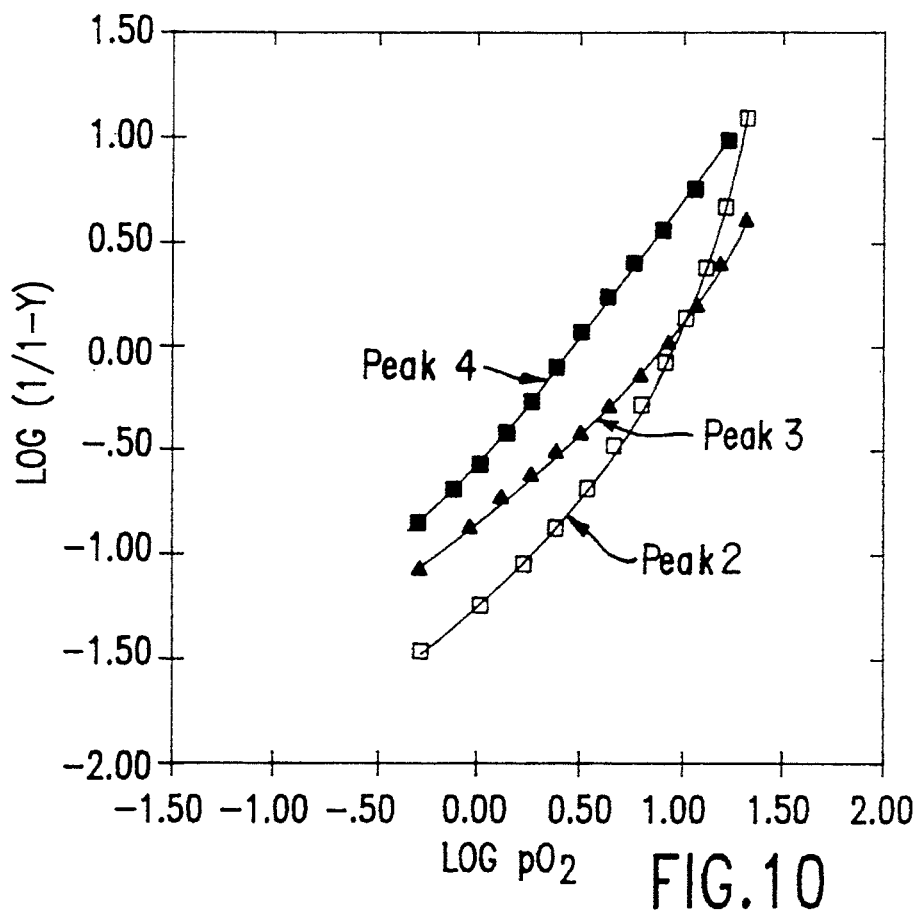
FIG. 10 shows oxygen affinity curves at pH 7.4 for peaks 2, 3, and 4 of BPC/EDC modified HbA at pH 6 at 20° C.
Figure 11:
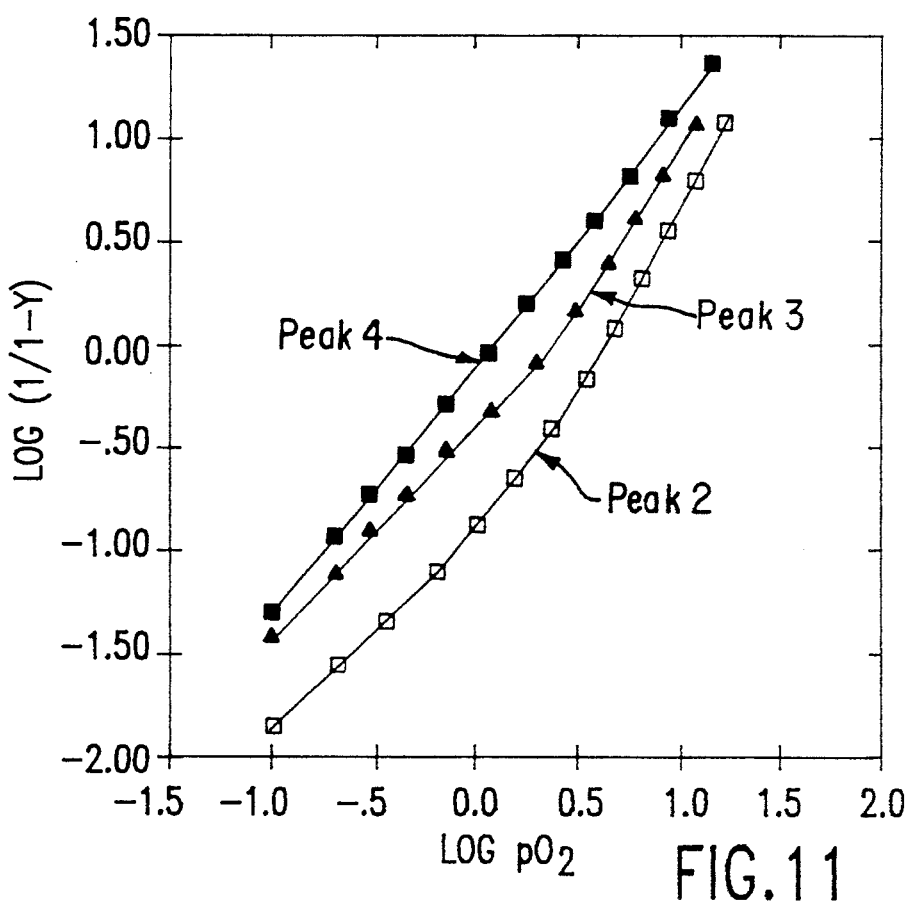
FIG. 11 shows oxygen affinity curves at pH 8.4 for peaks 2, 3, and 4 of BPC/EDC modified HbA at pH 6 at 20° C.

The anion-exchange profile (FIG. 5) suggests that the degree of modification of HbA with BPC increases from peak #2, through #3 to #4. FIGS. 10 and 11 show that increasing degrees of modification result in an increase in the oxygen affinity, and a decrease in the cooperativity of oxygen binding. These figures also show that the lower asymptotes diverge, while the upper asymptotes seem to converge. The additional binding of BPC residues thus increases the affinity of the deoxy HbA conformation for oxygen.

Figure 5:
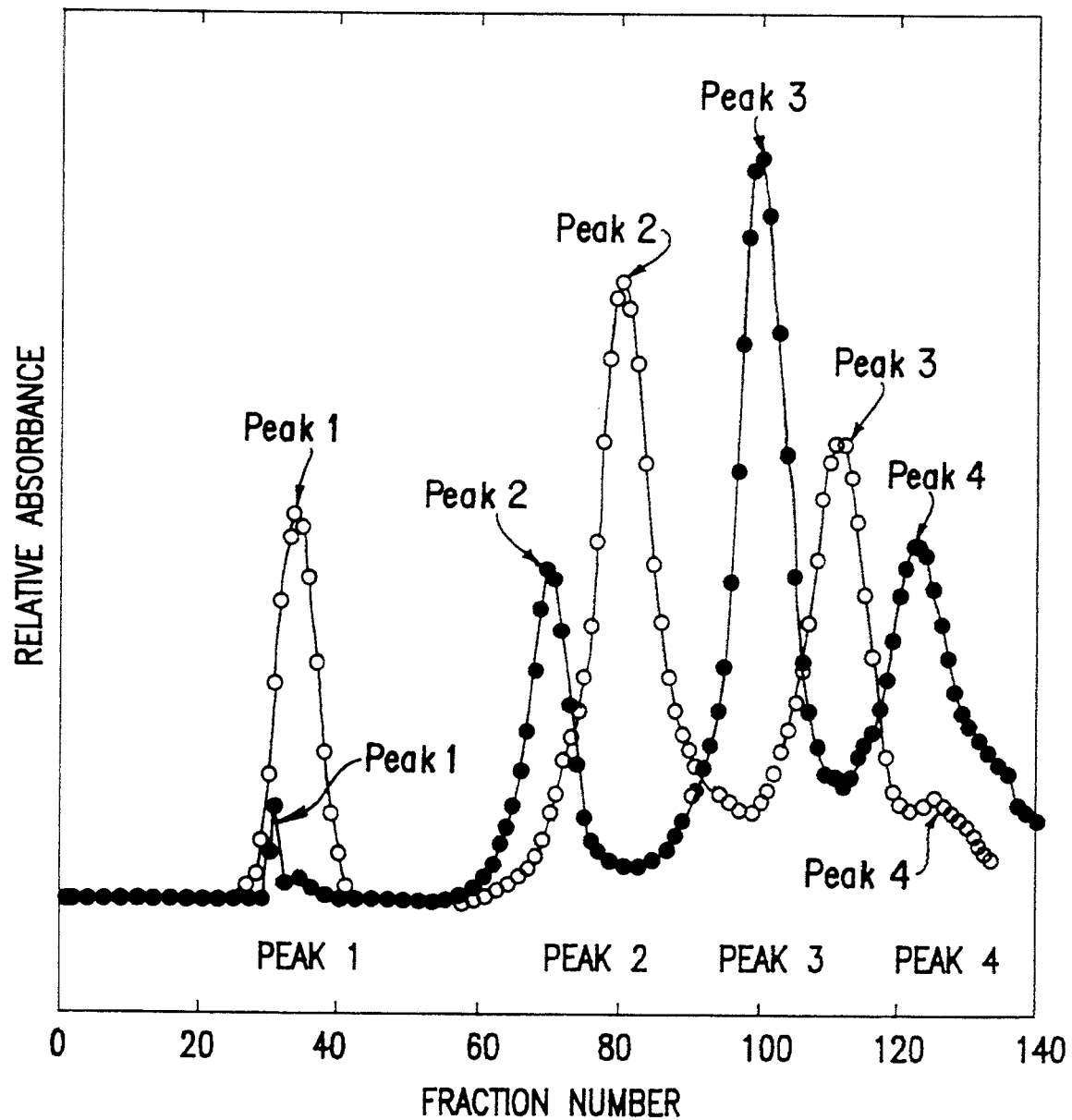
FIG. 5 shows a BPC/EDC modification elution profile samples prepared at ○-pH 8.0 under N$_2$ Atmosphere and ●-pH 6.0 under N$_2$ Atmosphere.
Figure 12:
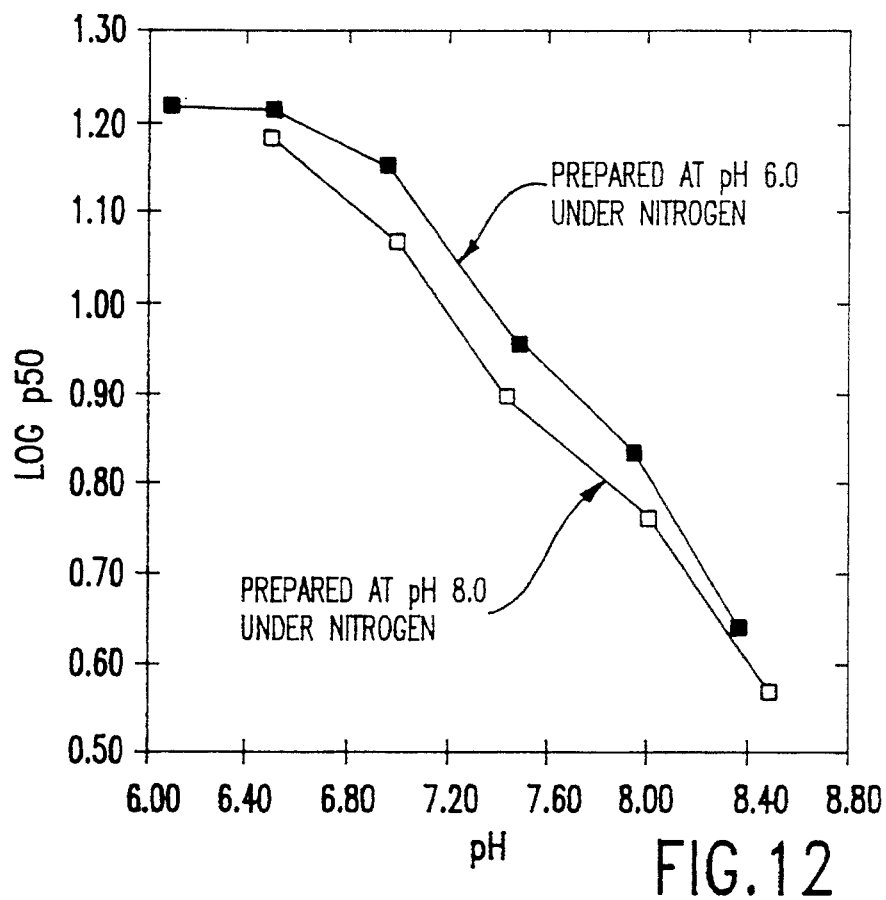
FIG. 12 shows a the dependency on pH of the oxygen affinity of isolated peak #2 of BPC/EDC treated HbA prepared at pH 6.0 and 8.0.
Figure 13:
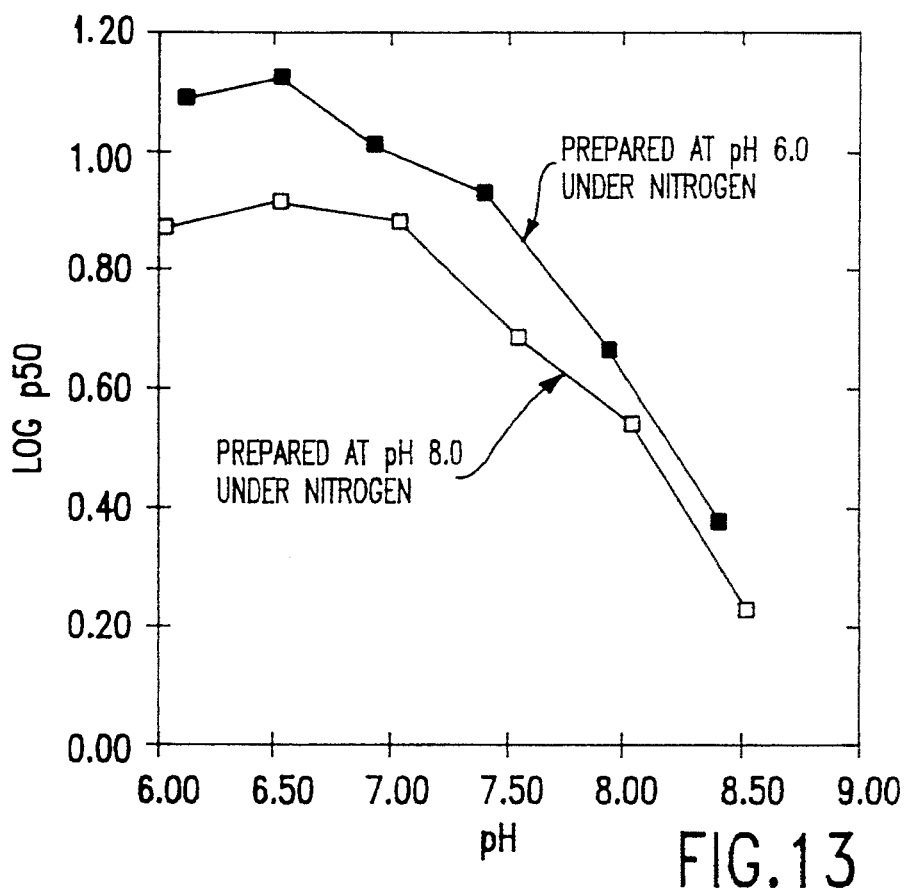
FIG. 13 shows the dependency on pH of the oxygen affinity of isolated peak #3 of BPC/EDC treated HbA prepared at pH 6.0 and 8.0.

The elution profile in FIG. 5 also shows that peaks #2 and #3, obtained after modification of HbA at pH 6 are structurally different from the peaks #2 and #3 obtained at pH 8. The data presented in FIGS. 12 and 13 shows these peaks are functionally different as well. Peak #2 prepared at pH 8 has a higher affinity for oxygen than Peak #2 prepared at pH 6 (FIG. 12). This difference is even more pronounced for peaks #3 prepared at pH 6 and pH 8 (FIG. 13). Finally it should be pointed out that the magnitude of the Bohr effect of peaks #2, #3 and #4 is very similar (FIG. 5). This demonstrates that the additional BPC-modifications in peak #3 and #4 have no effect on the observed Bohr effect.

The invention described and claimed herein is not to be limited in scope by the specific embodiments herein disclosed, since these embodiments are intended as illustrations of several aspects of the invention. Any equivalent embodiments are intended to be within the scope of this invention. Indeed various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. Stroma-free tetrameric mammalian hemoglobin having an affinity for oxygen which is lower than that of non-crosslinked hemoglobin A, and which is crosslinked with benzenepentacarboxylate, in which at least two carboxylate groups have been activated with an activating agent prior to reaction with the hemoglobin.

2. The stroma-free tetrameric hemoglobin according to claim 1 in which the hemoglobin is derived from a human.

3. The stroma-free tetrameric hemoglobin according to claim 1 in which the activating agent of the carboxylate is a carbodiimide.

4. The stroma-free tetrameric hemoglobin according to claim 3 in which the carbodiimide is 1-ethyl-3-(-3-dimethylaminopropyl)-carbodiimide.

5. The stroma-free tetrameric hemoglobin according to claim 1 in which the $P_{50}$ is at least twice as high as the $P_{50}$ of hemoglobin A when both of said $P_{50}$ values are measured under substantially the same conditions.

6. Stroma-free tetrameric mammalian hemoglobin having an affinity for oxygen which is lower than that of non-crosslinked hemoglobin A, and which is crosslinked with benzenepentacarboxylate, in which from about two to three carboxylate groups have been activated with a carbodiimide prior to reaction with the hemoglobin.

7. The stroma-free tetrameric hemoglobin according to claim 6 in which the hemoglobin is derived from a human.

8. The stroma-free tetrameric hemoglobin according to claim 6 in which the carbodiimide is 1-ethyl-3-(-3-dimethyl-aminopropyl)-carbodiimide.

9. A method for producing stroma-free crosslinked hemoglobin having an affinity for oxygen which is lower than that of non-crosslinked hemoglobin A, comprising:
 (a) crosslinking hemoglobin with benzenepentacarboxylate, in which at least two carboxylate groups have been activated with an activating agent prior to the crosslinking; and
 (b) isolating the crosslinked hemoglobin of step (a).

10. A method for producing stroma-free crosslinked hemoglobin having an affinity for oxygen which is lower than that of non-crosslinked hemoglobin A, comprising:
 (a) crosslinking hemoglobin with benzenepentacarboxylate, in which about two to three of the carboxylate groups have been activated with a carbodiimide prior to the crosslinking; and
 (b) isolating the crosslinked hemoglobin of step (a).

11. The method according to claim 10 in which the activation with a carbodiimide is done in the presence of catalase and EDTA.

12. The method according to claim 9 in which the activating agent is 1-ethyl-3-(3-dimethylaminopropyl)-carbodiimide.

13. The method according to claim 10 in which the carbodiimide is 1-ethyl-3-(3-dimethylaminopropyl)-carbodiimide.

14. The method according to claim 11 in which the carbodiimide is 1-ethyl-3-(3-dimethylaminopropyl)-carbodiimide.

15. The stroma-free tetrameric hemoglobin according to claim 4 in which the hemoglobin is derived from a human.

16. The stroma-free tetrameric hemoglobin according to claim 8 in which the hemoglobin is derived from a human.

17. The method according to claim 12 in which the hemoglobin is derived from a human.

* * * * *